(12) United States Patent
Arle et al.

(10) Patent No.: US 8,909,344 B2
(45) Date of Patent: Dec. 9, 2014

(54) HEAD WORN BRAIN STIMULATION DEVICE AND METHOD

(71) Applicants: Jeffrey Edward Arle, Concord, MA (US); Jay Lawrence Shils, Somerville, MA (US)

(72) Inventors: Jeffrey Edward Arle, Concord, MA (US); Jay Lawrence Shils, Somerville, MA (US)

( * ) Notice: Subject to any disclaimer, the term of this patent is extended or adjusted under 35 U.S.C. 154(b) by 0 days.

(21) Appl. No.: 13/788,555

(22) Filed: Mar. 7, 2013

(65) Prior Publication Data

US 2014/0257448 A1 Sep. 11, 2014

(51) Int. Cl.
*A61N 1/18* (2006.01)
*A61N 1/04* (2006.01)

(52) U.S. Cl.
CPC .................................... *A61N 1/0484* (2013.01)
USPC ............................................ 607/45; 607/139

(58) Field of Classification Search
None
See application file for complete search history.

(56) References Cited

U.S. PATENT DOCUMENTS

| | | | |
|---|---|---|---|
| 3,099,245 A | 7/1963 | Deaner | |
| 6,904,322 B2 * | 6/2005 | Katsnelson | 607/72 |
| 7,146,217 B2 * | 12/2006 | Firlik et al. | 607/45 |
| 7,303,578 B2 | 12/2007 | De Taboada et al. | |
| 7,315,761 B2 | 1/2008 | De Ridder | |
| 8,019,110 B1 | 9/2011 | Johnson | |
| 8,046,076 B2 | 10/2011 | Whitehurst et al. | |
| 8,316,467 B2 | 11/2012 | Foust et al. | |
| 8,380,318 B2 | 2/2013 | Kishawi et al. | |
| 8,504,166 B2 | 8/2013 | Lee et al. | |
| 8,620,441 B2 | 12/2013 | Greenberg et al. | |
| 2002/0128694 A1 | 9/2002 | Holsheimer | |
| 2005/0154426 A1 | 7/2005 | Boveja et al. | |
| 2006/0106430 A1 | 5/2006 | Fowler et al. | |
| 2006/0173510 A1 | 8/2006 | Besio et al. | |
| 2010/0036191 A1 | 2/2010 | Walter et al. | |
| 2010/0113959 A1 | 5/2010 | Pascual-Leone et al. | |
| 2011/0009920 A1 | 1/2011 | Whitehurst et al. | |
| 2011/0082326 A1 | 4/2011 | Mishelevich et al. | |
| 2011/0093033 A1 * | 4/2011 | Nekhendzy | 607/46 |
| 2011/0112602 A1 | 5/2011 | Lee et al. | |
| 2011/0137381 A1 | 6/2011 | Lee et al. | |
| 2011/0160524 A1 | 6/2011 | Ni et al. | |
| 2011/0288610 A1 | 11/2011 | Brocke | |
| 2012/0078319 A1 | 3/2012 | De Ridder | |
| 2012/0179076 A1 | 7/2012 | Bavelier et al. | |
| 2013/0204315 A1 * | 8/2013 | Wongsarnpigoon et al. | 607/45 |

FOREIGN PATENT DOCUMENTS

CN 202600904 12/2012

OTHER PUBLICATIONS

Finch, Caleb; The Neurobiology of Middle-Age Has Arrived; Neurobiology of Aging 30 (2009) pp. 515-520.
Hedden, Trey and Gabriela, John D.E.; Insights into the Ageing Mind: A View From Cognitive Neuroscience; Nature Reviews, Neuroscience, col. 5, Feb. 2004, pp. 87-97.

(Continued)

*Primary Examiner* — Brian T Gedeon

(57) ABSTRACT

A self-contained portable head worn device and methods to stimulate a portion of the brain of a wearer are presented. A first electrode is held by the head worn device against the scalp of the wearer in a first location and a second electrode is held against the scalp of the wearer in a second location. A pulse generator generates a first electric signal received by the first electrode and a second electric signal received by the second electrode. A power source is connected to the pulse generator.

5 Claims, 5 Drawing Sheets

(56) References Cited

OTHER PUBLICATIONS

Raffaele Nardone, et al; Effect of Transcranial Brain Stimulation for the Treatment of Alzheimer Disease: A Review; Hindawi Publishing Corporation; International Journal of Alzheimer's Disease; vol. 2012, Article ID 687909, 5 pages.

R. Ferrucci, F. Mameli, I. Guidi, et al.; Transcranial direct current stimulation improves recognition memory in Alzheimer disease; Neurology 2008;71;493-498 Published Online before print Jun. 4, 2008.

Bennett Eugene Postlethwaite; Fluid ability, crystallized ability, and performance across multiple domains: a meta-analysis; PhD diss., University of Iowa, 2011. http://ir.uiowa.edu/etd/1255.

P S Boggio, L P Khoury, D C S Martins, O E M S Martins de Macedo, Fregni; Temporal cortex direct current stimulation enhances performance on a visual recognition memory task in Alzheimer disease; J Neurol Neurosurg Psychiatry 2009;80:444-447. doi:10.1136/jnnp.2007.141853.

Mai Lu, T. Thorlin, Shoogo Ueno, and Mikael Persson; Comparison of Maximum Induced Current and Electric Field from Transcranial Direct Current and Magnetic Stimulations of a Human Head Model; Piers Online, vol. 3, No. 2, 2007; p. 178-183.

Bikson, Marom, and Rahman, ASIF, Origins of specificity during tDCS: anatomical, activity-selective, and input-bias mechanisms. Front Hum Neurosc 7 (2013). 1-5.

Jaberzadeh, Shapour, et al., Anodal transcranial pulsed current stimulation: A novel technique to enhance corticospinal excitability. Clin Neurophys 124 (2014). 344-351.

Fitzgerald, Paul B. Transcranial pulsed current stimulation: A new way forward? Clin Neurophys 124 (2014). 217-219.

Bikson, Marom, and Rahman, ASIF, Origins of specificity during tDCS: anatomical, activity-selective, and input-bias mechanisms. Fron Hum Neurosc. vol. 7 Oct. 2013, 1-5.

Jaberzadeh, Shapour, et al., Anodal transcranial pulsed current stimulation: A novel technique to enhance corticospinal excitability. Clin Neurophys 2014. 344-351.

\* cited by examiner

HEAD WORN BRAIN STIMULATION DEVICE AND METHOD

FIELD OF THE INVENTION

The present invention relates to cognitive brain function, and more particularly, is related to electromagnetic stimulation of the brain.

BACKGROUND OF THE INVENTION

In typical aging adults, functions related to Dorsal Lateral Prefrontal Cortex (DLPFC) activity decline. As seen in recent large longitudinal studies of intelligence and cognition, shown in FIG. 1, cognitive declines typically begin after the age of 50 or earlier, depending on the task.

Various techniques have been developed for electromagnetic stimulation of neural structures, including Transcranial Magnetic Stimulation (TMS), Deep Brain Stimulation (DBS), and transcranial Direct Current Stimulation (tDCS). These techniques have been applied for different functional and technical reasons. For example, stereotactic Transcranial Magnetic Stimulation (sTMS) has been used to provide neuromodulation of deep targets.

TMS uses electromagnetic induction to induce weak electric currents using a rapidly changing magnetic field. TMS devices use magnetic field stimulation of various target regions within the brain with magnetic coils placed in various positions around the brain of the patient. Such devices are typically large and stationary, using significant amounts of energy to generate appropriate magnetic fields. Furthermore, such devices typically require the patient to remain sufficiently stationary in relation to the magnetic coils to direct the magnetic fields to the targeted portion of the brain.

Transcranial direct current stimulation (tDCS) is a form of neurostimulation which uses constant, low current delivered through the scalp and skull to the brain area of interest via small electrodes. However, constant application of even a low current may cause irritation or burning of skin in contact with the electrodes.

Therefore, there is a need to address the above mentioned shortcomings.

SUMMARY OF THE INVENTION

Embodiments of the present invention provide a head worn brain stimulation device and method. Briefly described, the present invention is directed to a portable head worn device configured to stimulate a portion of the brain of a wearer. The device includes a first electrode configured to be held against the scalp of the wearer in a first location, and a second electrode configured to be held against the scalp of the wearer in a second location. A pulse generator is configured to generate a first electric signal received by the first electrode and a second electric signal received by the second electrode. A power source is connected to the pulse generator. The first electric signal and the second electric signal induce an electric current between the first electrode and the second electrode through the scalp of the wearer and the portion of the brain of the wearer.

A second aspect of the present invention is directed to a method for stimulating portions of the brain of a wearer of a wearable portable therapeutic device. The method includes the steps of positioning a first electrode against the skin of the wearer in the vicinity of one of either the left DLPFC or the right DLPFC, positioning a second electrode against the skin of the wearer, applying a first stimulation current to the first electrode, and applying a second stimulation current to the second electrode.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principals of the invention.

DETAILED DESCRIPTION

Figure 1:
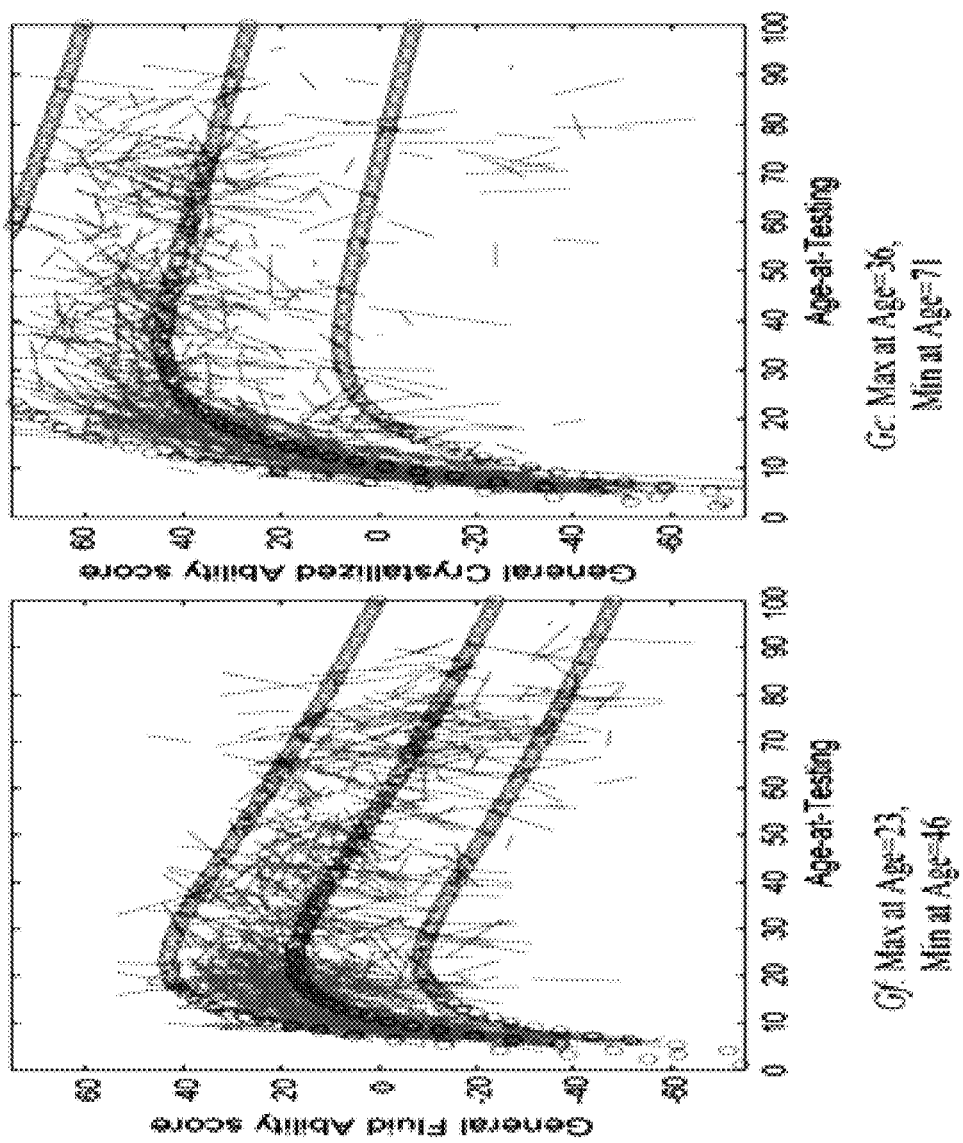
FIG. 1 includes two graphs displaying cognitive abilities of persons according to age.

Reference will now be made in detail to embodiments of the present invention, examples of which are illustrated in the accompanying drawings. Wherever possible, the same reference numbers are used in the drawings and the description to refer to the same or like parts.

Exemplary embodiments of the current invention provide a freely portable self-contained head worn device and methods for providing a painless, non-invasive way to help stimulate at least one area of the brain. For example, the stimulated area may be the DLPFC, which may be involved in memory maintenance, social intelligence, judgment, attention, reward evaluation, and an area that seems also to be important in controlling impulsivity and poor adjustments to new situations. The DLPFC is interconnected with other of brain connectivity that helps coordinate cognitive functions.

Embodiments of the head worn device provide a continuous, low frequency stimulation of the brain through the scalp and skull of the wearer. The device may be configured as, for example, a baseball cap or headband, among other configurations. The wearer typically does not experience sensation from electrical stimulation provided by the head worn device. Such undetectable stimulation may provide a slight modification to the threshold for activity of neurons in the DLPFC. The current provided by the head worn device is not sufficient to activate neurons receiving the current, but instead makes it more likely that the neurons retain their ability to be activated during normal brain activity. The head worn device may be used to maintain brain function of older wearers at levels more typical of younger persons, and extend these levels for a protracted time period.

Figure 3:
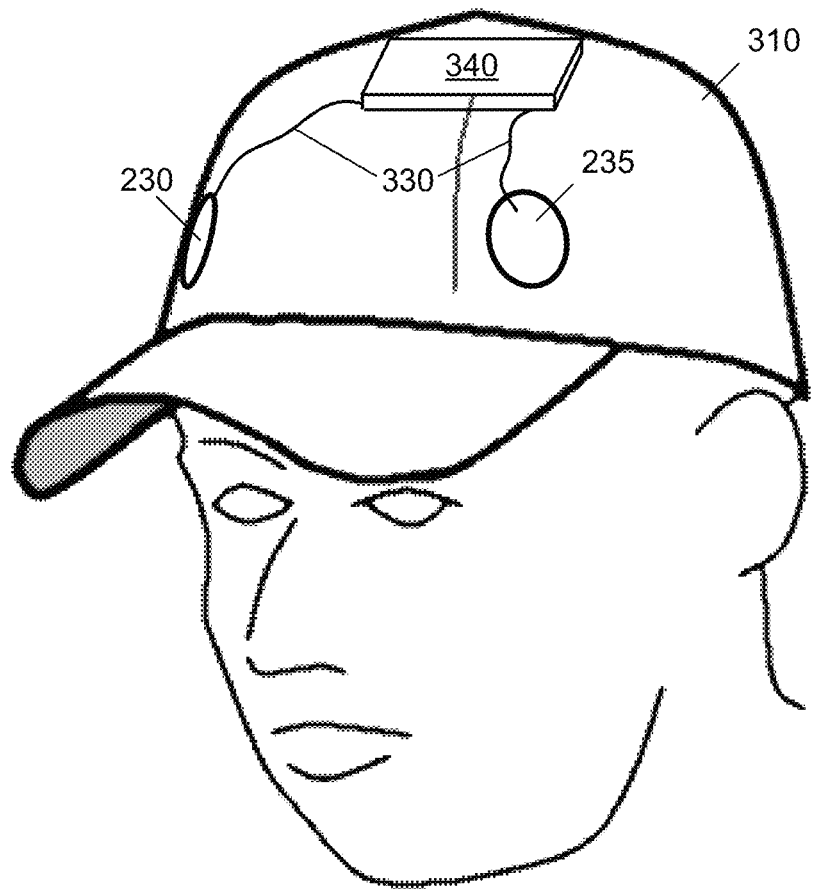
FIG. 3 is a schematic diagram depicting a first configuration of the head worn device of FIG. 2.

A first exemplary embodiment of a device under the present invention includes a head worn device, for example, a baseball cap 310, as shown in FIG. 3. The head worn device 310 may serve both to house electronic circuitry, and to hold electronic contacts, or electrodes, in position against the scalp of a wearer in a substantially stationary manner.

Figure 2:
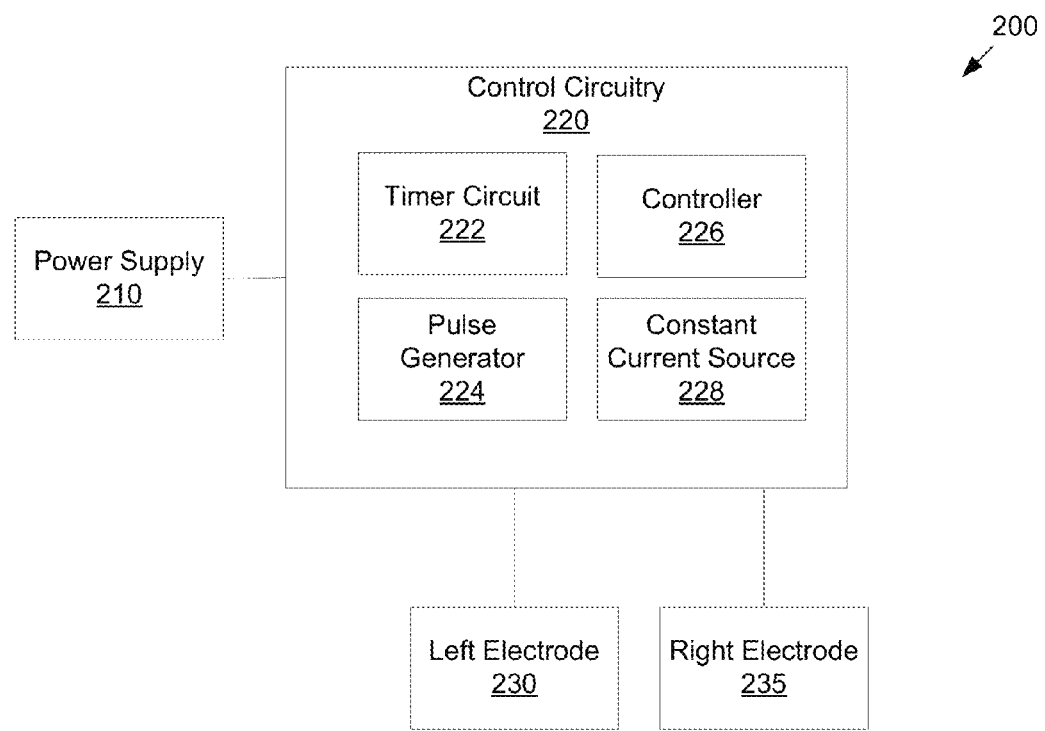
FIG. 2 is a block diagram of circuit components of a head worn device under the first embodiment.

FIG. 2 is a block diagram of circuit components under the first embodiment. The circuitry 200 may include a power supply 210, control circuitry 220, and electrodes 230, 235. The control circuitry is configured to provide a low current periodic waveform (electrical signal) to the electrodes 230, 235. The power supply 210 may be one or more chemical batteries, for example, but not limited to, an alkaline battery, and a lithium battery. Other technologies familiar to persons having ordinary skill in the art may be implemented for the power supply 210, for example, a solar cell or fuel cells. The power supply 210 provides power to the control circuitry 220. In the first embodiment, the control circuitry includes a timer circuit 222, a pulse generator 224, a controller 226, and a constant current source 228. The electrodes 230, 235 may be configured to either receive the electrical signal from the control circuitry 220 or to return the electrical signal received from another electrode back to the pulse generator 224 as the signal passes through the brain.

The controller 226 may serve as an interface to user controls, for example, a power switch, or a polarity selector (described further below). Other controls may include, but are not limited to, a frequency selector and/or a pulse shape selector. The controller 226 may be in electrical communication with the timer circuit 222 and/or the pulse generator 224. The pulse generator 224 shapes a low frequency periodic waveform, for example, a square wave pulse. However, other waveforms may also be used, for example, but not limited to, a sine wave, a sawtooth wave pulse, a triangular wave, a random wave, or a custom designed wave train. In addition, the pulse generator 224 may be configured to provide a direct current (DC) output, or a continuous periodic waveform, instead of intermittent pulses. The pulse generator 224 may be, for example, an astable pulse generator.

The timer circuit 222 determines the rate at which the control circuitry 220 delivers an electronic signal, for example, a pulse signal, to the electrodes 230, 235. The constant current source 228, for example, a Wilson current mirror, accepts the pulse signal as input from the pulse generator 224, and provides constant current pulse signals to the left electrode 230 and/or the right electrode 235. In general, the pulse signal delivered to the left electrode 230 has the opposite polarity of the pulse signal delivered to the right electrode 235. While a Wilson current mirror may be preferable since it works well with the high impedances that may be encountered in this embodiment, there is no objection to using other constant current sources or current drivers familiar to persons having ordinary skill in the art.

The control circuitry 220 is electrically connected to the left electrode 230 and the right electrode 235. The electrical connections may be wires, for example, integrated into a headband or a head covering portion of the head worn device 310 (FIG. 3). The control circuitry 220 may also control other elements, for example, a status LED to indicate operation of the device 310 (FIG. 3). The LED may be configured to blink or flash brighter at certain times, for example, indicating pulse signals being transmitted to the electrodes 230, 235.

The electrodes 230, 235 provide an area of electrical contact between the circuit 200 and skin of the user. The electrodes 230, 235 may be, for example but not limited to, steel discs with approximately a 1 cm diameter. While the first embodiment uses electrodes 230, 235 in the form of 1 cm stainless steel discs, other configurations of electrodes 230, 235 may also be used. For example, discs larger or smaller than 1 cm may be used. A larger surface area of the electrodes 230, 235 may be desirable to minimize the heating of the electrode by lowering the current density and the surface of the electrode in the event of an unintended current surge. In addition, electrodes 230, 235 may have shapes other than circular discs, for example, oval or rectangular shaped electrodes 230, 235 may be used, as well as other shapes. Further, any type of conductive material may be used in fabrication of the electrodes 230, 235. For example, a firm conductive metal, or a flexible conductive ceramic material may be used in such fabrication. The electrodes 230, 235 may be composed of compound materials, for example, a flexible material such as plastic or rubber may have a coating or wrapping of a conductive metal to provide a suitable contact area with the skin of the patient.

The electrodes 230, 235 may provide anodal or cathodal stimulation. The anodal stimulation uses a positive charge on the electrode, while cathodal stimulation uses a negative charge on the electrode. Simultaneous anodal and cathodal stimulation provides a current path through the scalp, skull, and brain between the positively charged electrode and the negatively charged electrode. The first embodiment includes a single cathode electrode and a single anode electrode. The cathode electrode may be positioned near the left DLPC and the anode electrode may be positioned near the right DLPC. However, alternative embodiments may have the cathode electrode positioned near the right DLPC and the anode electrode positioned near the left DLPC. In another alternative embodiment, the head worn device 310 (FIG. 3) may provide for one or more electrodes to be switched from anode to cathode, or from cathode to anode, for example, by a polarity switch or button connected to the control circuitry 220, for example, the controller 226.

In the first embodiment, the position of the electrodes 230, 235 is fixed within the head worn device 310 (FIG. 3). However, in alternative embodiments one or more of the electrodes 230, 235 may be relocatable within the head worn device 310 (FIG. 3), for example, to more precisely position the electrodes 230, 235 according to the specific needs of the wearer.

A second embodiment of the head worn device includes more than two electrodes. For example, the second embodiment may employ two or more cathode-anode pairs of electrodes, where each pair may be individually controlled for electrical parameters, for example, pulse shape, current amplitude, and pulse frequency. It should be noted that if there is at least one cathode and one electrode, there may be embodiments with any number of electrodes and cathodes, where there may be an unequal number of cathodes and anodes.

The controller 226 adjusts the constant current level, and in conjunction with the constant current source 228 ensures that the current level provided to the electrodes 230, 235 is limited to being below a safety threshold, for example, on the order of 1 microamp to 1 milliamp, although the present invention is not limited to this range. In addition, the circuitry 200 may be configured to provide a substantially constant current output level in the presence of variations of other factors detected by the control circuitry 220, for example, the amount of moisture and/or electrolytes present at the skin-electrode interface. This may be detected by a change in resistance in the circuit 200. The constant current driver 228 may adjust the current output in relation to variations in the load at the output of the circuit 200.

The controller 226 also ensures that the control circuitry 220 generates pulses within a desired parameter range. For example, it may be desirable to ensure that the maximum frequency is limited within the range of 0.2 Hz to 10 Hz, such as 1 Hz, although the present invention is not limited to this range. The circuit is further configured to deliver current below a threshold level. The threshold level is a current level sufficient to cause a neuron to fire an action potential. An exemplary sub-threshold level may be a current level in the range of 1 microamp to 1 milliamp, although the present invention is not limited to this range.

Other embodiments are possible. For example, a third embodiment may be similar to the first embodiment and/or the second embodiment, adding a feedback path where return current is received and monitored by the controller 226 for various characteristics, for example, pulse shape, pulse spreading, and/or pulse amplitude. The controller 226 may then modify one or more of the timer circuitry 220, the pulse generator 224, and/or the constant current source 228 accordingly, to produce a desired change in the received current.

FIG. 3 is a schematic diagram of the head worn device 310 as worn by a wearer. The electrodes 230, 235 may be positioned adjacent to the DLPFC, or they may be positioned non-adjacent to the DLPFC, but merely in the general vicinity of the DLPFC. The electrodes 230, 235 are held in place by the head worn device 310. The electrodes 230, 235 may be attached to the baseball cap 310, for example, using a hook and loop fastener, snaps, or other such detachable/re-attachable connector, so the electrodes 230, 235 may be moved to various locations within the baseball cap 310. Such a connector may be non-electrically conducting. There may be padding behind the electrodes 230, 235 to add pressure holding the electrodes against the head of the wearer. Of course, other attachment methods, including non-detachable attachment methods such as sewing or gluing, may be used, as will be familiar to persons having ordinary skill in the art.

The electrodes 230, 235 are electrically connected by wires 330 to the control circuit 220 (FIG. 2) contained within a housing 340. The housing 340 may be attached, for example, sewn, to fabric of the baseball cap 310, or otherwise contained within the baseball cap 310 by other attachment means, for example, within a pouch or a pocket in the baseball cap 310. The wires 330 may be integrated into the fabric of the hat or covered, for example, by fabric tape or strips within the hat. It should be noted that while FIG. 3 shows the electrodes 230, 235 and housing 340 as being visible from the outside of the baseball cap 310 for illustrative purposes, in practice the electrodes 230, 235 and housing 340 are typically concealed by the fabric of the baseball cap 310.

The head worn device 310 may integrally include the control circuitry 220 (FIG. 2) and power supply 210. However, alternative embodiments may have the control circuitry 220 and/or the power supply 210 as not being integral to the head worn device 310, but rather separately housed, for example, clipped onto the clothing or a belt of the wearer, or carried in a pocket of the wearer. In such embodiments, the separately housed control circuitry 220 and/or power supply 210 may be connected to the head worn device 310 via a connecting wire, where the connecting wire may be detachable, for example, using a connector plug and socket configuration familiar to persons having ordinary skill in the art.

Method

Figure 4:
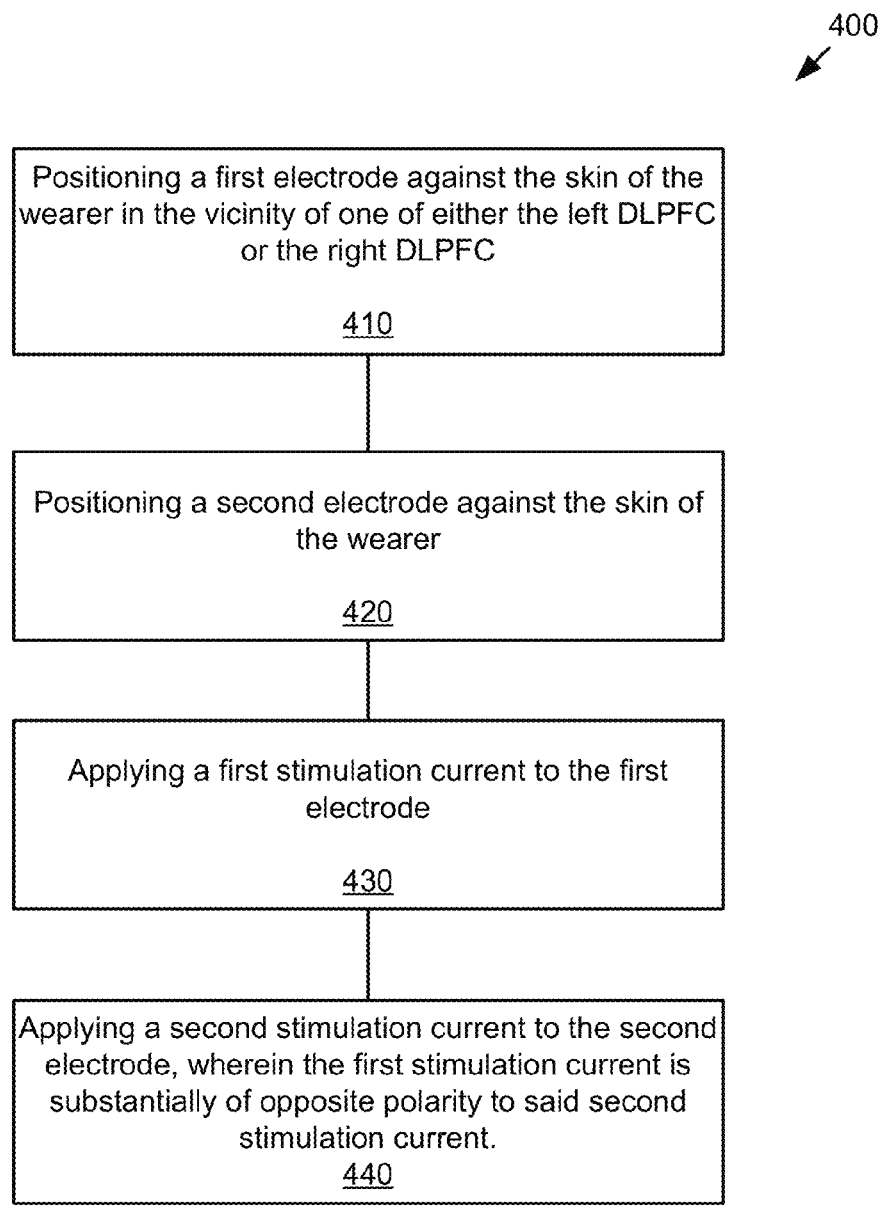
FIG. 4 is a flowchart of an exemplary embodiment of a method for stimulating portions of the brain of a wearer of the head worn portable therapeutic device of FIG. 2 and FIG. 3.

FIG. 4 is a flowchart 400 of an exemplary embodiment of a method for stimulating portions of a brain of a wearer of the wearable portable therapeutic device of FIG. 3. It should be noted that any process descriptions or blocks in flow charts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

A first electrode is positioned against the skin of the wearer in the vicinity of one of either the left DLPFC or the right DLPFC, as shown by block 410. While it may generally be preferable to position the first electrode as close as possible to the left DLPFC, there may be instances where it is desirable to locate the first electrode nearby the left DLPFC, but not at the nearest point. For example, the hair patterns or cranial shape of a particular wearer may provide a better electrical connection for the electrode at a position nearby the left DLPFC other than the nearest location to the left DLPFC.

A second electrode is positioned against the skin of the wearer, as shown by block 420. The second electrode is preferably positioned adjacent to or nearby the right DLPFC. However, there is no objection to locating the second electrode elsewhere on the scalp of the wearer as long as the positioning facilitates current flow between the first electrode and second electrode through the left DLPFC.

A first stimulation current is applied to the first electrode, as shown by block 430. As described above, the current is preferably a low amplitude square wave having a frequency below 1 Hz, although the current invention is not limited by this range. A similar second stimulation current is applied to the second electrode, as shown by block 440. The first stimulation current may be substantially of opposite polarity to the second stimulation current, thereby inducing a flow of current between the first electrode and the second electrode through the brain of the wearer. However, the second stimulation current may be substantially different from the first stimulation current, for example, in amplitude or shape, or even a null current where the first stimulation current applied to the first electrode substantially drives most or all of the current through the brain of the wearer.

Figure 5:
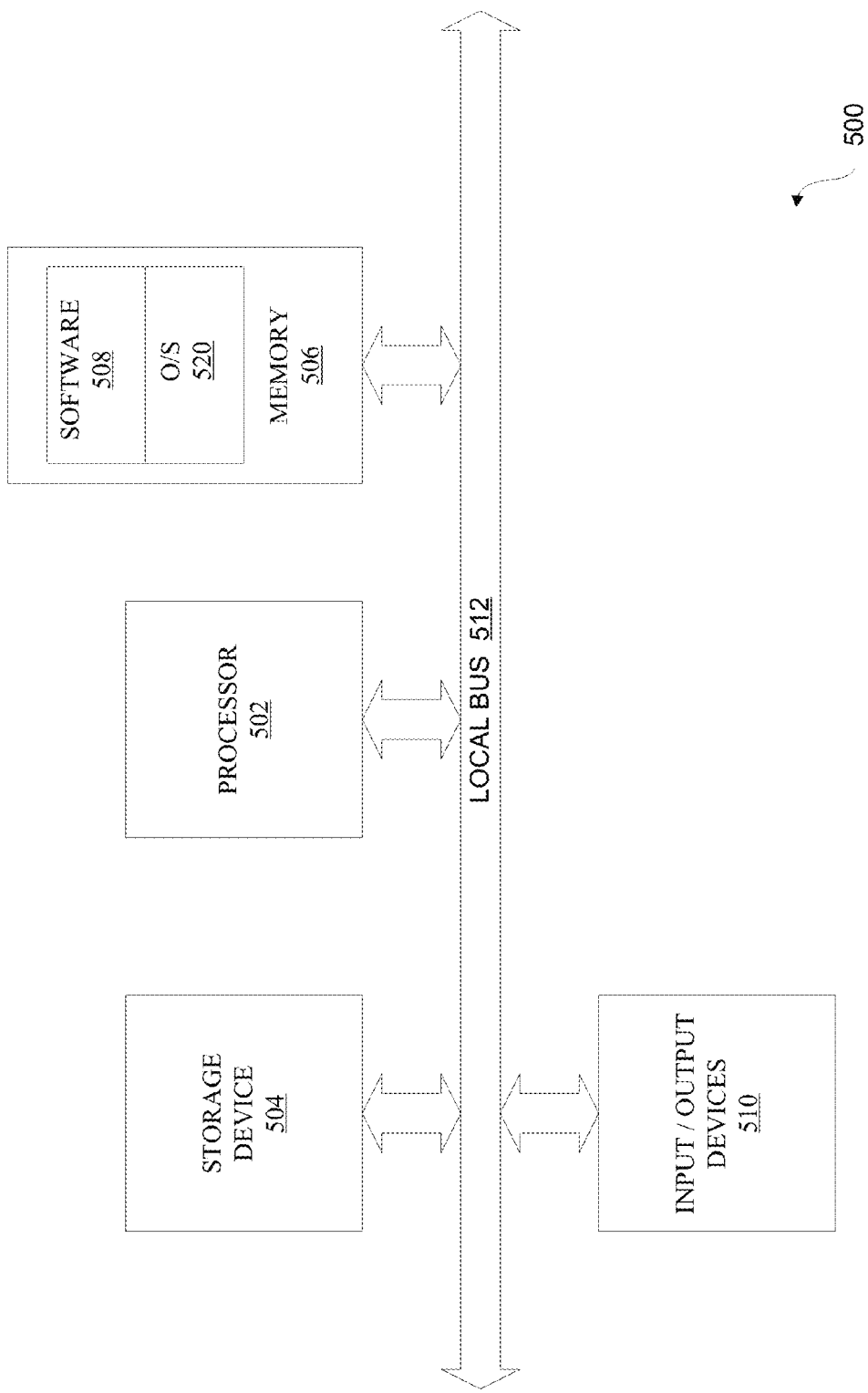
FIG. 5 is a schematic diagram illustrating an example of a generalized system for executing functionality of the present invention.

The control circuitry 220 (FIG. 2) described in detail above may be a computer system 500, an example of which is shown in the schematic diagram of FIG. 5. The system 500 may contain a processor 502, a storage device 504, a memory 506 having software 508 stored therein that defines the above-mentioned functionality, input and output (I/O) devices 510 (or peripherals), and a local bus, or local interface 512 allowing for communication within the system 500. The local interface 512 can be, for example but not limited to, one or more buses or other wired or wireless connections, as is known in the art. The local interface 512 may have additional elements, which are omitted for simplicity, such as controllers, buffers (caches), drivers, repeaters, and receivers, to enable communications. Further, the local interface 512 may include address, control, and/or data connections to enable appropriate communications among the aforementioned components.

The processor 502 is a hardware device for executing software, particularly that stored in the memory 506. The processor 502 can be any custom made or commercially available single core or multi-core processor, a central processing unit (CPU), an auxiliary processor among several processors associated with the present system 500, a semiconductor based microprocessor (in the form of a microchip or chip set), a macroprocessor, an ASIC, or generally any device for executing software instructions. The processor 502 may be incorporated by and execute functions of the control circuitry 220 (FIG. 2).

The memory 506 can include any one or combination of volatile memory elements (e.g., random access memory (RAM, such as DRAM, SRAM, SDRAM, etc.)) and nonvolatile memory elements (e.g., ROM, flash memory, EEPROM etc.). Moreover, the memory 506 may incorporate electronic, magnetic, optical, and/or other types of storage media. Note that the memory 506 can have a distributed architecture, where various components are situated remotely from one another, but can be accessed by the processor 502.

The software 508 defines functionality performed by the system 500, in accordance with the present invention. The software 508 in the memory 506 may include one or more separate programs, each of which contains an ordered listing of executable instructions for implementing logical functions of the system 500, as described below. The memory 506 may contain an operating system (O/S) 520. The operating system essentially controls the execution of programs within the system 500 and provides scheduling, input-output control, file and data management, memory management, and communication control and related services.

The I/O devices 510 include electrodes described above, and may also include input devices, for example but not limited to, buttons, switches, dials, touchpads, etc. Furthermore, the I/O devices 510 may also include output devices, for example but not limited to, an LED, character display, audio transducer such as a buzzer, etc. Finally, the I/O devices 510 may further include devices that communicate via both inputs and outputs, for instance but not limited to, a modulator/demodulator (modem; for accessing another device, system, or network), a radio frequency (RF) or other transceiver, or other device.

When the system 500 is in operation, the processor 502 is configured to execute the software 508 stored within the memory 506, to communicate data to and from the memory 506, and to generally control operations of the system 500 pursuant to the software 508, as explained above. The memory 506 may be configured to store parameters monitored during operation for feedback operations, as described above. Such parameters may also be stored for later recovery, for example, to monitor usage patterns of a wearer of the head worn device.

It will be apparent to those skilled in the art that various modifications and variations can be made to the structure of the present invention without departing from the scope or spirit of the invention. For example, while the head worn device has been described as a baseball cap or a headband, there is no objection to embodiments of the device incorporated into other types of headwear, such as traditional headwear, casual headwear, sports headwear, helmets, caps, bandanas, berets, scarves, turbans, wigs and hairpieces, veils, uniforms, and outerwear. In general, the head worn device may be incorporated into any head worn housing that maintains contact between the scalp of the wearer and the electrodes. In view of the foregoing, it is intended that the present invention cover modifications and variations of this invention provided they fall within the scope of the following claims and their equivalents.

What is claimed is:

1. A method for ameliorating decline in cognitive ability by stimulating portions of a brain of a wearer of a wearable portable head worn device, comprising the steps of:
    positioning a first electrode against the skin of the wearer in the vicinity of one of either the left or the right dorsal lateral prefrontal cortex;
    positioning a second electrode against the skin of the wearer;
    applying a first stimulation current to the first electrode;
    applying a second stimulation current to the second electrode;
    and
    limiting said first stimulation current and/or said second stimulation to induce a resulting current to a portion of the brain of the wearer below a current level sufficient to activate a neuron receiving said resulting current.

2. The method of claim 1, wherein applying said first stimulation current and said second stimulation current further comprising the step of providing a periodic square wave stimulus to the first electrode and the second electrode, of which the period of said periodic stimulus is random.

3. The method of claim 1, wherein applying a stimulation current further comprising the step of providing a direct current to the first electrode and the second electrode.

4. The method of claim 1, wherein said stimulation current is substantially of opposite polarity to said second stimulation current.

5. The method of claim 1, wherein applying said first stimulation current and said second stimulation current further comprising the step of providing a low frequency periodic stimulus to the first electrode and the second electrode, wherein said frequency comprises 10 Hz or less.

* * * * *